(12) United States Patent
Benchikh et al.

(10) Patent No.: US 8,530,177 B2
(45) Date of Patent: Sep. 10, 2013

(54) CHLORAL HYDRATE DETECTION

(75) Inventors: Elouard Benchikh, Crumlin (GB); Ivan McConnell, Crumlin (GB); Peter Fitzgerald, Crumlin (GB); Philip Lowry, Crumlin (GB)

(73) Assignee: Randox Laboratories Limited (GB)

( * ) Notice: Subject to any disclaimer, the term of this patent is extended or adjusted under 35 U.S.C. 154(b) by 203 days.

(21) Appl. No.: 13/171,599

(22) Filed: Jun. 29, 2011

(65) Prior Publication Data

US 2012/0003674 A1 Jan. 5, 2012

(30) Foreign Application Priority Data

Jun. 30, 2010 (EP) ..................................... 10168015

(51) Int. Cl.
*G01N 33/94* (2006.01)
*C07K 16/00* (2006.01)

(52) U.S. Cl.
USPC ........................... 435/7.92; 435/7.1; 436/501

(58) Field of Classification Search
None
See application file for complete search history.

(56) References Cited

PUBLICATIONS

Engelhart, D. A., et al., "Unusual Death Attributed to the Combined Effects of Chloral Hydrate, Lidocaine, and Nitrous Oxide," Journal of Analytical Toxicology, 22: 246-247 (1998).
Gaulier, J. M., et al., "Fatal Intoxications with Chloral Hydrate," Journal of Forensic Sciences, 46(6): 1507-1509 (2001).
European Search Report dated Nov. 10, 2010 from corresponding European Application No. 10168015.5.
Arndt, T., et al., "False-positive Ethyl Glucuronide Immunoassay Screening Associated With Chloral Hydrate Medication As Confirmed by LC-MS/MS and Self-Medication," Forensic Science International, 184:e27-e29 (2009).
Breimer, D. D., "Clinical Pharmacokinetics of Hypnotics," Clinical Pharmacokinetics, 2: 93-109 (1977).
Delinsky, A.D., et al., "A Review of Analytical Methods for the Determination of Trichloroethylene and its Major Metabolites Chloral Hydrate, Trichloroacetic Acid and Dichloroacetic Acid," Biomedical Chromatography, 19:617-639 (2005).
Heller, P. F., et al., "Chloral Hydrate Overdose: Trichloroethanol Detection by Gas Chromatography/Mass Spectrometry," Forensic Science International, 52:231-234 (1992).
Ikeda, M., et al., "Determination of Urochloralic Acid, the Glucuronic Acid Conjugate of Trichloroethanol, By Gas Chromatography with Electron-Capture Detection and Its Application to Urine, Plasma and Liver," Journal of Chromatography 307:111-119 (1984).
Kim, D., et al., "Comparative Metabolism and Disposition of Trichloroethylene in *Cyp2e1*-/- and Wild-Type Mice," Drug Metabolism and Disposition, 34:2020-2027 (2006).
Lash, L. H., et al., "Metabolis of Trichloroethylene," Environmental Health Perspectives, 108 (Suppl 2) 177-200 (2000).
Merdink, J. L., et al., "Kinetics of Chloral Hydrate and Its Metabolites in Male Human Volunteers," Toxicology 245:130-140 (2008).
Ogata, M., et al., "Simple Microdetermination of Trichloroethanol Glucuronide and Trichloroacetic Acid in Urine," Int. Arch. Arbeitsmed, 32:203-215 (1974).
Schmitt, T. C., "Determination of Chloral Hydrate and Its Metabolites in Blood Plasma by Capillary Gas Chromatography with Electron Capture Detection," Journal of Chromatography B, 780:217-224(20O2).
Stenner, R.D., et al., "Enterohepatic Recirculation of Trichloroethanol Glucuronide as a Significant Source of Trichloroacetic Acid," Drug Metabolism and Disposition, 25:(5)529-535 (1997).

*Primary Examiner* — Shafiqul Haq
*Assistant Examiner* — Galina Yakovleva
(74) *Attorney, Agent, or Firm* — McDermott Will & Emery LLP

(57) ABSTRACT

The invention relates to an immunoassay method and kit for the indirect detection of chloral hydrate. The invention is underpinned by a novel immunogen that produces an antibody that is specific for the chloral hydrate metabolite trichloroethanol glucuronide. Detection and quantification of trichloroethanol glucuronide has important applications in clinical toxicology, drug facilitated crime, water testing and solvent exposure.

5 Claims, 5 Drawing Sheets

Immunogen II

Chloral hydrate

Trichloroacetic acid 2,2,2-Trichloroethanol

Trichloroethanol glucuronide

CHLORAL HYDRATE DETECTION

RELATED APPLICATION

Figure 1:
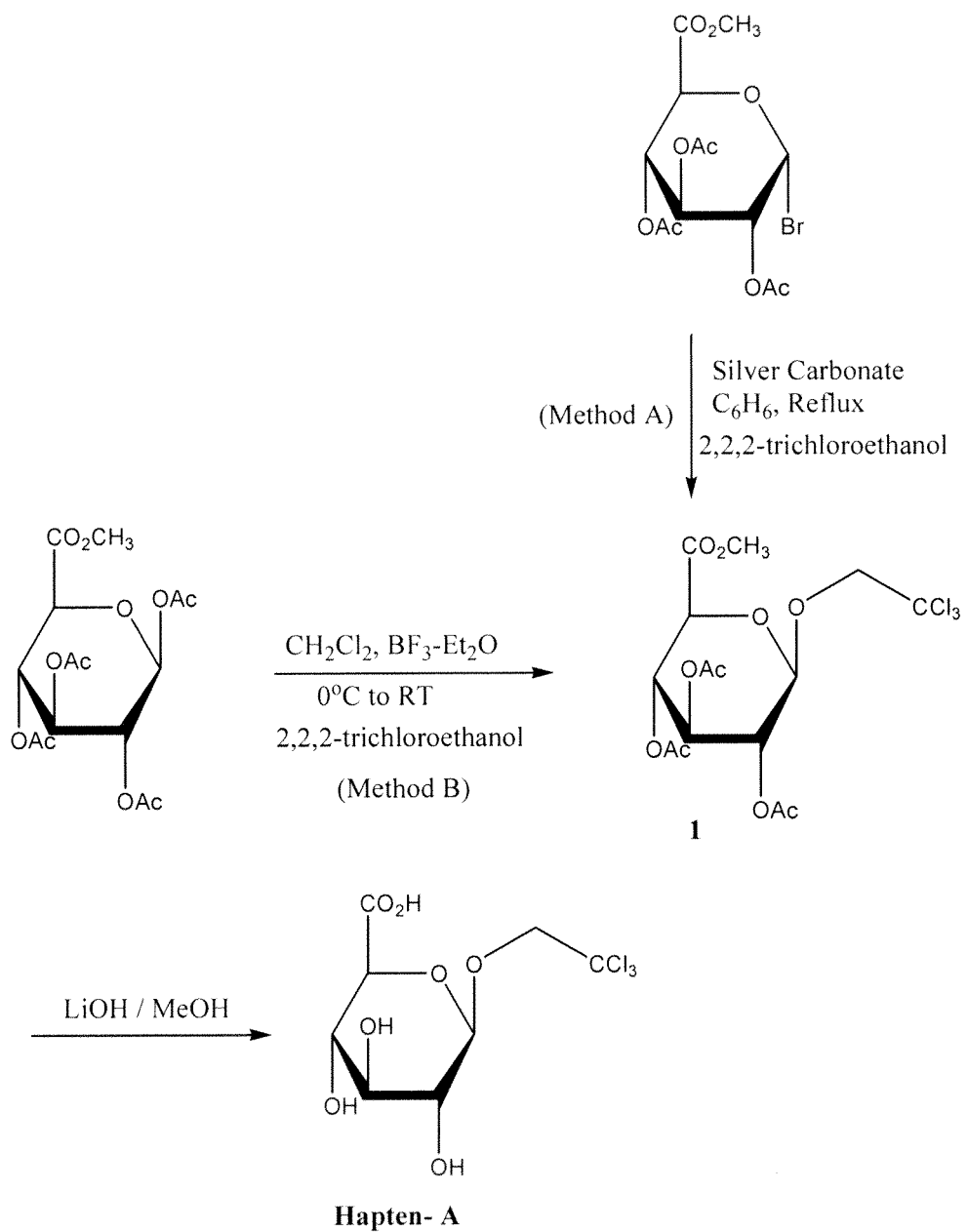

This application claims the benefit under 35 USC §119(b) of European Patent Application No. 10168015.5 filed Jun. 30, 2010, the entire contents of which are incorporated herein by reference.

BACKGROUND TO THE INVENTION

Analytical detection and quantification of drugs of abuse, therapeutic drugs, animal drug residues and environmental contaminants such as pesticides and industrial chemicals is an important and widespread commercial practice, and can be laboratory or field-based. The analytical equipment used in the laboratory and field can be the same, but field-based methods are generally more restricted due to size and analytical capabilities. For example, although portable formats have been constructed, commonly used analytical methods for precise quantification are gas chromatography (GC) and liquid chromatography (LC) often linked to mass spectrometers (to give GC-MS and LC-MS, respectively), and are restricted to use in the laboratory. The major alternatives to the chromatographic-based methods make use of the interaction of molecules through chemical reactions or chemical complexation, the latter typified by antibody-ligand binding. The main advantages of these chemical 'binding' methods compared to chromatographic methods are their relative low cost, simplicity and portability, enabling use in the field.

Chloral hydrate, 2,2,2-trichloroethanediol, is used as a sedative, in anaesthesia and as a chemical precursor in synthetic organic chemistry. Its use to combat insomnia can lead to addiction and overdose (Gaullier et at 2001; Engelhart et at 1998). Chloral hydrate overdose is often detected by the Fujiwara reaction which detects the metabolite 2,2,2-trichloroethanol, followed by quantification using GC-MS. Its sedative properties have been exploited for illegal use; when mixed with alcohol it produces the tasteless and odorless "knockout drops" or "Mickey Finn", historically used to facilitate robbery. Discussion of drug facilitated rape (DFR) routinely includes reference to chloral hydrate. However, definitive proof of its use in DFR is generally lacking which implies either that such use is rare or that there are issues with its detection. Chloral hydrate is rapidly metabolized (Breimer 1977), the main metabolites being trichloroethanol, trichloroethanol glucuronide (TCG) and trichloroacetic acid, with respective half-lives of 7-10 hours, 7-10 hours and approximately 4 days (PharmGKB: The Pharmacogenetics and Pharmacogenomics Knowledge Base, Chloral Hydrate, Accession ID:PA448925). During the twenty four hours following a single oral dose of chloral hydrate approximately 0.7% is excreted in the urine as trichloroethanol and 28% as TCG (Disposition of Toxic Drugs and Chemicals in Man, eighth edition). Analytical methods used to detect and quantify the metabolites of chloral hydrate include GC fitted with an ECD detector (Breimer 1977; Ikeda et al 1984) and the Fujiwara reaction plus GC-MS (Heller et al. 1992).

Chloral hydrate is a disinfection by-product (DBP) in the industrial chlorination of water, attributed to the reaction of chlorine with trace organic matter such as humic acid, and it has been classified as a possible human carcinogen by the US Environmental Protection Agency (EPA) and Health Canada. The US EPA has approved a method using Gas Chromatography-Electron Capture Detection (GC-ECD) for its quantification and Health Canada suggests a Tolerable Daily Intake (TDI) of 0.3 mg/d for the average person (Health Canada, Guidance on Chloral Hydrate in Drinking Water). Levels in drinking water have been measured at 1.2-8.4 ng/ml (maximum 23 ng/ml) in Canada, and 1.7-2.5 ng/ml (maximum 46 ng/ml) in the United States. Trichloroethylene is an industrial solvent used extensively in metal cleaning and degreasing and human exposure to the chemical can occur through contaminated air, drinking water or food. Upon inhalation or ingestion, the chemical is rapidly metabolized via two routes; glutathione conjugation is the minor route, oxidation by cytochrome P450 enzymes the major route. The principal oxidative route produces the epoxide which is rapidly transformed into chloral/chloral hydrate, followed by synthesis of trichloroethanol, and finally trichloroethanol glucuronide formation (L. H. Lash et al 2000). The glucuronide is found in the urine of humans or other mammals exposed to or administered trichloroethylene (Lash et al 2000; Stenner et al 1997, Kim and Ghanayem 2006) and has been linked to autoimmune disease.

To the inventors' know ledge, an immunoassay for the detection of chloral hydrate use and generation has never been described even though an immunoassay based test would be desirable. It is highly likely that this is due to the small size of the molecule and its metabolites, trichloroethanol, trichloroethanol glucuronide and trichloroacetic acid, which present difficulties for antibody development; for example, such small molecules present a small target epitope for an antibody, potentially compromising resultant antibody specificity and titre.

Thus, provision of an antibody-based assay for suspected chloral hydrate induced DFR, excessive chlorine in water and suspected trichloroethylene exposure would be a rapid and cheap alternative to current detection methods. Furthermore, an off-the shelf device, such as a dip-stick, would enable individuals or environmental monitoring agencies to detect chloral hydrate, chlorine and trichloroethylene indirectly by measurement of TCG in urine samples.

BIBLIOGRAPHY

Breimer D. D. (1977). *Clin. Pharmacokin.*, 2: 93-109.
Engelhart D. A. et at (1998). *J. Anal. Toxicol.*, 22: 246-247.
Gaullier J. M. et at (2001). *J. Forensic Sci.*, 46: 1507-1509.
Heller P. et al (1992). *Forens. Sci. Int.*, 52: 231-234
Ikeda M. et al (1984). *J. Chroniatogr.*, 307: 111-119.
Lash L. H. et at (2000). *Env. Health Perspectives*, 108: 177-200.
Stenner et at (1997). *Drug Metab. Dispos.*, 25: 529-535;
Kim D. and Ghanayem B. (2006). *Drug Metab. Dispos.* 34: 2020-2027
Arndt T. et at (2009). *Forens. Sci. Int.*, 184:E27-E29.

SUMMARY OF THE INVENTION

Described herein is the first known immunoassay that indirectly confirms the presence or use of chloral hydrate. Because of the rapid metabolism of chloral hydrate, the inventors developed using novel immunogens and a novel antibody, a surrogate immunoassay for its detection and quantification which targets the metabolite TCG. The antibody of the invention is surprisingly specific for TCG. The use of a TCG-specific antibody in an immunoassay format overcomes resource and practical limitations associated with previously described analytical methods used to detect chloral hydrate and its metabolites, enabling its application in diverse areas such as DFR, water-testing and environmental toxicology.

DRAWINGS

FIG. 1 Preparation of Hapten A

Figure 2:
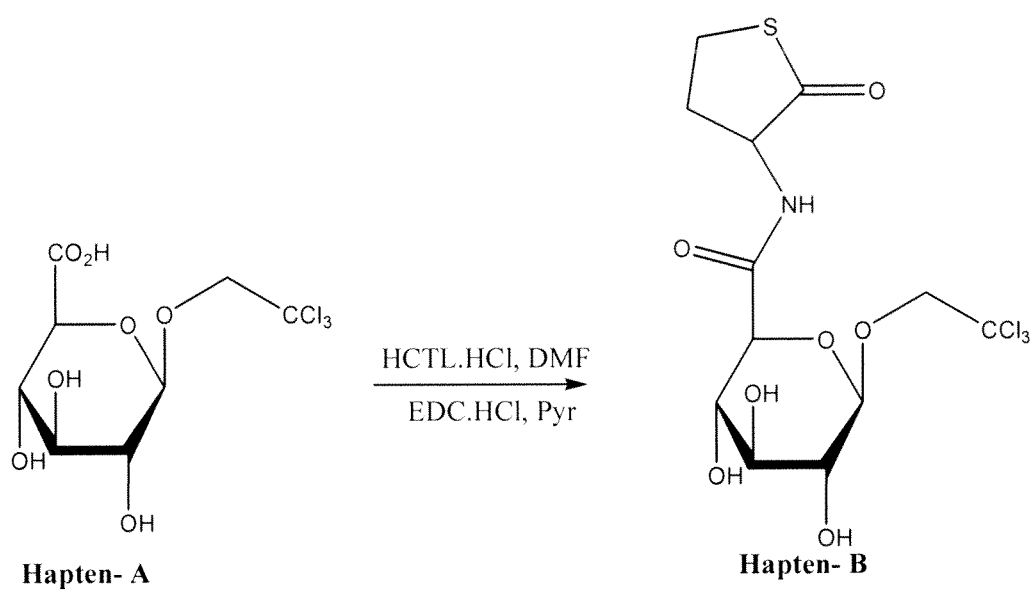

FIG. 2 Preparation of Hapten B

Figure 3:
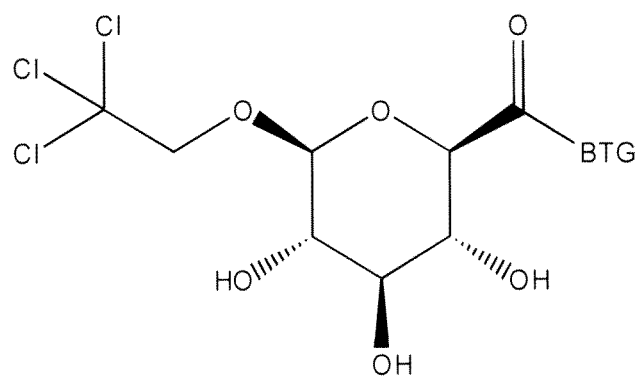

FIG. 3 Immunogen II

Figure 4:
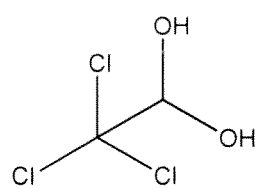
Figure 4:
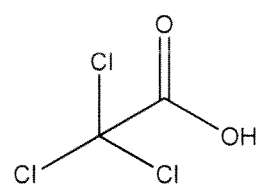
Figure 4:
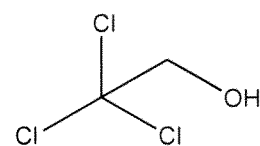
Figure 4:
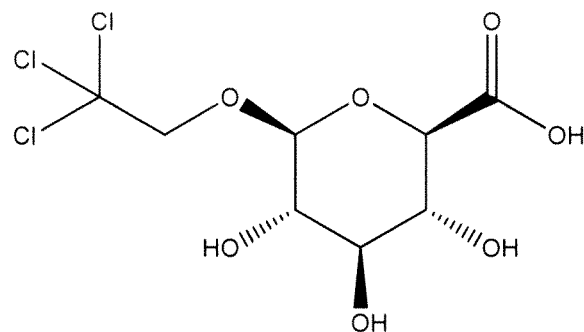

FIG. 4 The structures of chloral hydrate, trichloroacetic acid, 2,2,2-trichloroethanol and trichloroethanol glucuronide.

Figure 5:
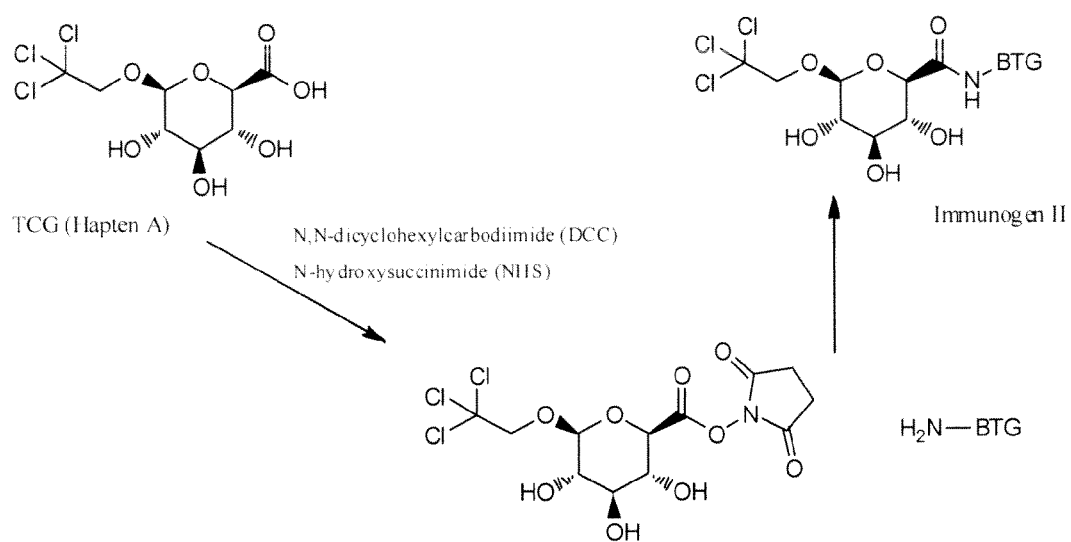

FIG. 5 Preparation of Immunogen II by conjugation of Hapten A to BTG using N,N -dicyclohexylcarbodiimide (DCC) and N-hydroxysuccinimide (NHS).

DETAILED DESCRIPTION OF THE INVENTION

A first aspect of the invention is an immunogen of the structure (structure 1)

Structure 1

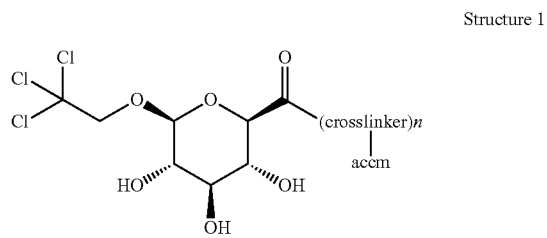

where n=0 or 1. When n=1, the crosslinker joins the carbonyl substituent of the tetrahydropyran ring to an antigenicity-conferring carrier material (accm). The crosslinker is a group that links the hapten to the accm. The hapten of the current invention is the trichloroethanol glucuronide moiety of Structure 1 which is linked to either the crosslinker or to the accm. The crosslinker, is preferably —X—Y-Z-, where X is a heteroatom, preferably nitrogen, oxygen or sulphur: Y is a $C_1$-$C_{10}$, preferably a $C_2$-$C_6$, substituted or unsubstituted straight chain alkylene moiety, or arylene moiety; Z (before conjugation with the accm) is selected from a carboxy, a dithiopyridyl, a maleimide, an amino, a hydroxyl, a thiol, a thioester or an aldehyde moiety, most preferably a carboxy moiety.

The preferred immunogen is where n=0 i.e. the preferred immunogen is TCG directly attached to the accm, A preferred immunogen of the invention is Immunogen II (Example 5), shown in FIG. 5 and schematically (without the amide linkage) in FIG. 3.

The accm can be any material that makes the hapten-accm molecule immunogenic. Suitable accms commonly contain poly(amino acid) segments. For example the accm can be a protein, a glycoprotein, a protein fragment, a synthetic polypeptide or a semi-synthetic polypeptide. Suitable accms include, but are not limited to, bovine serum albumin (BSA), egg ovalbumin, bovine gamma globulin, bovine thyroglobulin (BTG) and keyhole limpet haemocyanin (KLH). The accm is optionally selected from bovine serum albumin (BSA) or bovine thyroglobulin (BTG). A preferred accm is bovine thyroglobulin (BTG).

Alternatively, synthetic poly(amino acids) having a sufficient number of available amino groups, such as lysine, may be employed, as may other synthetic or natural polymeric materials bearing reactive functional groups. In particular, carbohydrates, yeasts or polysaccharides may be conjugated to the hapten to produce an immunogen. The haptens can also be coupled to a detectable labelling agent such as an enzyme (for example, horseradish peroxidase), a substance having fluorescent properties or a radioactive label for the preparation of conjugates (or detection reagents) for use in the immunoassays. The fluorescent substance may be, for example, a monovalent residue of fluorescein or a derivative thereof. Immunogen formation involves conventional conjugation methods.

It will be appreciated that where n=0, the preparation of an immunogen by conjugation of the hapten to the accm may be carried out in a number of ways, depending on the hapten and accm in question. For example, without limiting the options thereto, the hapten may be derivatized prior to conjugation to the accm; or the accm may be derivatized prior to conjugation to the hapten; or both the hapten and the accm may be derivatized prior to conjugation. Preferably, the hapten is derivatized prior to conjugation with the accm. For example, without limiting the invention thereto, the hapten may be derivatized so as to convert the carboxyl group of the hapten into an amine reactive ester group. The amine reactive ester group will then react with an amine group on the accm to form the immunogen comprising a hapten-accm conjugate directly linked via an amide (peptide) bond. Suitable derivatizing agents include, but are not limited to, N,N-dicyclohexylcarbodiimide (DCC), 1-ethyl-3-[3-dimethylaminopropyl]carbodiimide hydrochloride (EDC), N-hydroxysuccinimide (NHS), and N-hydroxysulfosuccinimide (sulfo-NHS), and combinations thereof. A preferred combination of derivatizing agents is N,N-dicyclohexylcarbodiimide (DCC) and N-hydroxysuccinimide (NHS).

A second aspect of the invention is an antibody that specifically binds to an epitope of TCG. The antibody is suitable for use in detecting TCG in an in vitro sample taken from a patient. The antibody is preferably raised against an immunogen of structure 1. As would be understood by the skilled man in the art, the term "specifically" implies that the antibody of the invention binds to TCG and not to molecules comprising molecular sub-structures of TCG, for example, ethyl glucuronide which contains the sugar ring of TCG or trichloroacetic acid which contains the trichloromethyl moiety of TCG. It is proposed that the epitope of TCG recognised by the antibody comprises the trichloromethyl substituted hydroxytetrahydropyran moiety of TCG (i.e. the trichloroethanol glucuronide moiety). The antibody can be a monoclonal antibody, but is preferably a polyclonal antibody.

A further aspect of the invention is a method of confirming ingestion of chloral hydrate by an individual, the method comprising contacting an in vitro sample taken from the individual with a conjugate (such as TCG-UKP—see Example 6), and an antibody that binds to an epitope of TCG, detecting the bound conjugate, and deducing by comparison with a suitable cut-off value the presence or absence of chloral hydrate.

Another aspect of the invention is a method of detecting and/or quantifying TCG in an individual, the method comprising contacting an in vitro sample taken from the individual with a conjugate, and the antibody of either of claims 5 or 6, detecting the bound conjugate, and deducing from calibrator values the presence or amount of TCG. The exact quantification of TCG, unlike the semi-quantitative method that uses a cut-off value, allows, in conjunction with an approximate time of ingestion, an estimate of the amount of chloral hydrate ingested to be calculated. This is achieved using the half-life value of chloral hydrate and the ratio of TCG to chloral hydrate.

The sample can be an) peripheral biological fluid but is preferably plasma, serum or urine, most preferably urine. The conjugates of the method are made up of haptens attached to labelling agents. The haptens of the conjugates are molecules that can bind to the antibodies of the method. The ability of the conjugate to bind to the antibody of the invention enables it to displace TCG which is the basis of the competitive immunoassay: other immunoassay formats such as the indirect method can also be implemented. The use of haptens, conjugates and antibodies in the context of immunoassays is well known in the art. Preferably, the labelling agent of the conjugates is selected from an enzyme, a luminescent substance, a radioactive substance, or a mixture thereof. More preferably, the labelling agent is an enzyme, preferably a peroxidase, most preferably horseradish peroxidase (HRP). Alternatively, or additionally, the luminescent substance may be a bioluminescent, chemiluminescent or fluorescent material.

Also described is a kit for detecting the presence or use of chloral hydrate in an individual, the use of chlorination products in drinking water supplies and trichloroethylene exposure in individuals, the kit comprising the antibody which binds to an epitope of TCG and a conjugate. The kit may optionally include instructions for the use of said antibodies for detecting TCG. The conjugate is preferably a derivative of TCG such as TCG-HRP. Alternatively, drinking water supplies can be analysed for chloral hydrate directly by forming and detecting and measuring TCG in situ. This would comprise taking a sample of drinking water (the solution) and synthesizing TCG in situ either enzymatically (using a uridine 5'-diphospho-glucuronosyltransferase) or through chemical derivitazation.

Another aspect of the invention is a kit for detecting and/or quantifying TCG, the kit including an antibody that binds to an epitope of TCG and a conjugate. The conjugate is preferably a derivative of TCG such as TCG-HRP. The kit may optionally include instructions for the use of said antibodies for detecting TCG. The kit may further include calibrators.

The inventors have conveniently overcome the difficulties associated with developing an immunoassay based test using such a small molecule, by developing an antibody that recognizes TCG. Therefore, advantageously, herein is described, for the first time, an antibody which enables the provision of an immunoassay for the indirect detection of chloral hydrate generation and use.

Methods and Results
Preparation of Haptens, Immunogens and Conjugates

Although haptens provide defined structural epitopes, they are not in themselves immunogenic and therefore need to be conjugated to carrier materials, which will elicit an immunogenic response when administered to a host animal. Appropriate carrier materials commonly contain poly (amino acid) segments and include polypeptides, proteins and glycoproteins. Illustrative examples of useful carrier materials are bovine serum albumin (BSA), egg ovalbumin, bovine gamma globulin, bovine thyroglobulin (BTG), keyhole limpet haemocyanin (KLH) etc. Alternatively, synthetic poly(amino acids) having a sufficient number of available amino groups, such as lysine, may be employed, as may other synthetic or natural polymeric materials bearing reactive functional groups. In particular, carbohydrates, yeasts or polysaccharides may be conjugated to the hapten to produce an immunogen. The haptens can also be coupled to a detectable labelling agent such as an enzyme (for example, horseradish peroxidase), a substance having fluorescent properties or a radioactive label for the preparation of conjugates (or detection reagents) for use in the immunoassays. The fluorescent substance may be, for example, a monovalent residue of fluorescein or a derivative thereof. Immunogen formation involves conventional conjugation methods. For example, when using N,N-dicyclohexylcarbodiimide (DCC) and N-hydroxysuccinimide (NHS), the oxygen of the hydroxyl group of the carboxylic acid group of TCG combines first with DCC and then NHS to form an activated ester with a powerful leaving group. Nucleophilic attack on the carbonyl of the activated ester by an amine group of the protein (BSA or BTG), results in an amide bond and formation of the immunogen, as shown in FIG. 5. In order to confirm that adequate conjugation of hapten to carrier material has been achieved, prior to immunization, each immunogen is evaluated using matrix-assisted UV laser desorption/ionization time-of-flight mass spectroscopy (MALDI-TOF MS).

Procedure for MALDI-TOF Analysis of Immunogens.

MALDI-TOF mass spectrometry was performed using a Voyager STR Bio-spectrometry Research Station laser-desorption mass spectrometer coupled with delayed extraction. An aliquot of each sample to be analysed was diluted in 0.1% aqueous trifluoroacetic acid (TFA) to create 1 mg/ml sample solutions. Aliquots (1 µl) were analysed using a matrix of Sinapinic acid and bovine serum albumin (Fluka) was used as an external calibrant.

Preparation of Antisera

In order to generate polyclonal antisera, the immunogen of the present invention is mixed with Freund's Adjuvant and the mixture is injected into a host animal, such as rabbit, sheep, mouse, guinea pig or horse. Further injections (boosts) are made and serum is sampled for evaluation of the antibody titre. When the optimal titre has been attained, the host animal is bled to yield a suitable volume of specific antiserum. The degree of antibody purification required depends on the intended application. For many purposes, there is no requirement for purification, however, in other cases, such as where the antibody is to be immobilized on a solid support, purification steps can be taken to remove undesired material and eliminate non-specific binding.

Immunoassay Development

The process of developing an immunoassay is well known to the person skilled in the art. Briefly, for a competitive immunoassay in which the target analyte is a non-immunogenic molecule commonly referred to as a hapten, the following process is conducted: antibodies are produced by immunizing an animal, preferably a mammalian animal, by repeated administration of an immunogen. The serum from the immunized animal is collected when the antibody titre is sufficiently high. A conjugate is added to a sample containing the target analyte and the raised antibodies, and the conjugate and analyte compete for binding to the antibodies. The process may comprise fixing said serum antibodies to a backing substrate such as a polystyrene solid support or a biochip. The antibodies can be polyclonal or monoclonal. However, if the polyclonal antibody is specific to TCG and sufficiently sensitive then the additional development and higher costs required for monoclonal antibody production are unnecessary. The signal emitted in the immunoassay is proportionate to the amount of conjugate bound to the antibodies which in turn is inversely proportionate to the analyte concentration. The signal is detected and then semi-quantified (exceeds a cut-off level) or quantified by comparison with calibrator(s).

EXAMPLE 1

Preparation of 1-O-trichloroethyl-2,3,4-tri-O-acetyl-α-D-glucopyranuronic acid methyl ester 1

Method A
To a solution of acetobromo-α-D-glucuronic acid methyl ester (5.96 g, 0.015 mol) in anhydrous benzene (200 ml) was added Silver carbonate (4.14 g, 0.015 mol) and 2,2,2-trichloroethanol (142 ml). The mixture was then heated at reflux for 4 hours and cooled at room temperature. The reaction was filtered and the filtrate was concentrated to dryness. The residue obtained was purified by chromatography on silica gel using a mixture of hexane-ethyl acetate (7/3)(v/v) to give acetobromo-α-D-glucuronic acid methyl ester (3.0 g) and the 1-O-trichloroethyl-2,3,4-tri-O-acetyl-α-D-glucopyranuronic acid methyl ester 1 (1.5 g) as a white powder solid Method B
$BF_3$-$Et_2O$ (15 ml) was added dropwise to a cooled solution at 0° C. of 1,2,3,4-tetra-O-acetyl-β-D-glucopyranuronic acid methyl ester (11.23 g, 0.03 mol) and 2,2,2-trichloroethanol (20 ml) in anhydrous dichloromethane (250 ml) under inert atmosphere. The mixture was stirred at room temperature overnight and then washed with 1N HCl (100 ml), water (100 ml) and brine (100 ml). The organic phase was dried over sodium sulphate, filtered and concentrated to dryness. 1-O-trichloroethyl-2,3,4-tri-O-acetyl-α-D-glucopyranuronic acid methyl ester 1 (8.95 g) was obtained after recrystallization of the crude product from ether.

EXAMPLE 2

Preparation of Trichloroethyl Glucuronide (Hapten A)

To a solution of 1-O-trichloroethyl-2,3,4-tri-O-acetyl-α-D-glucopyranuronic acid methyl ester 1 (5 g, 10.7 mM) in a mixture of methanol (90 ml) and water (10 ml) was added at 0° C. solid Lithium hydroxide (2.25 g, 53.7 mM) and the mixture was stirred at room temperature overnight. TLC indicated reaction to be completed. The methanol was removed under vacuum, water (100 ml) was added, the mixture was then neutralized to pH 7 by a solution of HCl (1N). The solution was evaporated to dryness and the solid obtained was suspended in methanol/chloroform (1:4) and stirred for seven hours at room temperature. The insoluble salts were removed by filtration and the solution was evaporated to dryness to give Hapten A (3.1 g) as a white solid.

EXAMPLE 3

Preparation of Trichloroethyl Glucuronide Homocysteine Thiolactone (Hapten B)

To a solution under nitrogen of TCG (Hapten A) (1.25 g, 3.83 mM) in dry pyridine (25 ml) was added homocysteine thiolactone hydrochloride (590 mg, 3.84 mM) and EDC hydrochloride (885 mg, 4.6 mM) and the mixture was stirred overnight at room temperature. Pyridine was removed under vacuum and the residue obtained purified by flash chromatography on silica gel using 20% methanol/80% chloroform to afford 750 mg of the pure trichloroethyl glucuronide homocysteine thiolactone (Hapten B) as an off-white foamy solid.

EXAMPLE 4

Conjugation of Hapten A to BSA (Immunogen I)

To a solution of TCG (Hapten A) (40.0 mg, 0.12 mmol) in DMF (1.0 ml) was added N,N-dicyclohexylcarbodiimide (DCC) (26.2 mg, 0.123 mmol) and N-hydroxysuccinimide (14.13 m, 0.123 mmol) and the mixture was stirred at room temperature overnight. The dicyclohexylurea formed was removed by filtration and the solution was added dropwise to a solution of BSA (100 mg, 1.5 µmol) in 50 mM sodium bicarbonate solution (pH 8.5) (10 ml). The mixture was then stirred overnight at 4° C. The solution was then dialyzed against 50 mM phosphate buffer pH 7.2 (3 changes) for 24 hours at 4° C., and freeze-dried. MALDI results showed 29.92 molecules of TCG (Hapten A) had been conjugated to one molecule of BSA.

EXAMPLE 5

Conjugation of Hapten A to BTG (Immunogen II)

To a solution of TCG (Hapten A) (65.75 mg, 0.202 mmol) in DMF (1.0 ml) was added N,N-dicyclohexylcarbodiimide (DCC) (45.8 mg, 0.222 mmol) and N-hydroxysuccinimide (25.54 mg, 0.222 mmol) and the mixture was stirred at room temperature overnight. The dicyclohexylurea formed was removed by filtration and the solution was added dropwise to a solution of BTG (150 mg) in 50 mM sodium bicarbonate solution (pH 8.5) (10 ml). The mixture was then stirred overnight at 4° C. The solution was then dialyzed against 50 mM phosphate buffer pH 7.2 (3 changes) for 24 hours at 4° C., and freeze-dried. The reaction mechanism is illustrated, in brief, in FIG. 5.

EXAMPLE 6

Conjugation of Hapten A to HRP

EDC hydrochloride (10 mg) was dissolved in water (0.5 ml) and immediately added to a solution of TCG (Hapten A) (2 mg) in DMF (0.2 ml), After mixing, this solution was added dropwise to a solution of HRP (20 mg) in water (1 ml). Sulfo-NHS (5 mg) was added and the reaction mixture was incubated in the dark at room temperature overnight. Excess hapten was removed with double PD-10 columns (Pharmacia) in series, pre-equilibrated with PBS at pH 7.2. The hapten-HRP conjugate was then dialyzed overnight against 10 L of PBS at pH 7.2 at 4° C.

EXAMPLE 7

Conjugation of Hapten B to Maleimide-Modified HRP

Trichloroethyl glucuronide homocysteine thiolactone (Hapten B) (2 mg) was dissolved in a mixture of DMF/water (100 µl) and to this solution was added potassium hydroxide (2M) (10 µl). The mixture was allowed to stand for 10 minutes. Phosphate buffer (100 µl) was added to quench the reaction and the pH was adjusted to 7 by the addition of 0.1M HCl. This solution was added dropwise to maleimide-modified HRP (20 mg) dissolved in phosphate buffer (1 ml) and the solution stirred at 4° C. overnight (protected from light). Excess hapten was removed with double PD-10 columns (Pharmacia) in series, pre-equilibrated with PBS at pH 7.2. The hapten-HRP conjugate was then dialyzed with 10 L of PBS at pH 7.2 at 4° C.

EXAMPLE 8

Development of an ELISA for TCG

TCG was coupled to bovine thyroglobulin (Immunogen II, Example 5). The resulting immunogen was administered to adult sheep on a monthly basis to provide target-specific polyclonal antisera. IgG was extracted from the antisera via caprylic acid/ammonium sulphate precipitation of immunoglobulin. Microtitre plates (Thermo Scientific, 468667) were coated with antibody (125 µl) in coating buffer (10 mM Tris pH 8.5) at 37° C. for 2 hours. Antibody was coated at 1.25 µg/ml. The plates were then washed. 50 µl of sample/standard (trichloroethyl glucuronide, Randox LK811; chloral hydrate, Sigma C8383-100 g; trichloroacetic acid, Fisher Scientific T/3000/50; ETG, Randox LK589) was added to the appropriate wells in triplicate, followed by 75 µl of hapten A-HRP conjugate at ¼K and incubated at 25° C. for 1 hour. The plates were then washed and 125 µl of TMB (Randox, 4380-15) was added to each well and left at room temperature for 20 mins in the dark. The reaction was stopped using 125 µl of 0.2M sulphuric acid. The absorbances were read at 450 nm with an ELISA microplate reader (BIO-TEK Instruments, Elx800) and the means calculated. Antibody specificity and sensitivity were then determined.

The inventors were alerted to the strong possibility that the antibody would recognize ethyl glucuronide, a metabolite of ethanol. Such concerns originated from the disclosure that an ethyl glucuronide antibody in a commercial assay was found to cross-react with what was inferred to be TCG (Arndt et al 2009). If a reverse cross-reactivity phenomenon occurred with the current invention (i.e. the TCG antibody binding to ethyl glucuronide) the chloral hydrate immunoassay would not be fit for purpose due to the social prevalence of alcohol ingestion. However, as can be seen from Table 1, ethyl glucuronide does not cross-react with the antibody of the invention, attesting to the antibody's surprisingly unique specificity.

Results

Competitive ELISA results in the Table 1 below highlight the specificity of the antibody of the invention towards TCG.

TABLE 1

| Cross-reactivity and specificity data for the antibody of the invention | | | | | | | | |
|---|---|---|---|---|---|---|---|---|
| TCG | | Chloral Hydrate | | Trichloroacetic Acid | | EtG | | |
| Standard (ng/ml) | $A_{450}$ | % $B/B_0$ | Standard (ng/ml) | $A_{450}$ | % $B/B_0$ | $A_{450}$ | % $B/B_0$ | $A_{450}$ | % $B/B_0$ |
| 0 | 1.516 | 100 | 0 | 1.523 | 100 | 1.504 | 100 | 1.364 | 100 |
| 1.25 | 1.313 | 86.6 | 31.25 | 1.457 | 95.7 | 1.372 | 91.2 | 1.183 | 86.7 |
| 2.5 | 1.228 | 81.0 | 62.5 | 1.516 | 99.5 | 1.391 | 92.5 | 1.144 | 83.9 |
| 5 | 1.061 | 70.0 | 125 | 1.455 | 95.5 | 1.389 | 92.4 | 1.157 | 84.8 |
| 10 | 0.872 | 57.5 | 250 | 1.324 | 86.9 | 1.312 | 87.2 | 1.130 | 82.8 |
| 20 | 0.641 | 42.3 | 500 | 1.359 | 89.2 | 1.284 | 85.4 | 1.094 | 80.2 |
| 40 | 0.465 | 30.7 | 1000 | 1.277 | 83.8 | 1.230 | 81.8 | 1.031 | 75.6 |
| 80 | 0.373 | 24.6 | 2000 | 1.195 | 78.5 | 1.094 | 72.7 | 0.950 | 69.6 |
| $IC_{50}$ | 13.724 | | $IC_{50}$ | >>2000 | | >>2000 | | >>2000 | |
| % CR | 100 | | % CR | <<0.69 | | <<0.69 | | <<0.69 | |

$A_{450}$ = absorbance at 450 nm; B = absorbance at 450 nm at x ng/ml standard concentration
$B_0$ = absorbance at 450 nm at 0 ng/ml standard concentration; $IC_{50}$ (ng/ml) = standard concentration which produces 50% $B/B_0$; % CR = percentage cross-reactivity based on 100% specificity to TCG

The invention claimed is:

1. A method of detecting and/or quantifying trichloroethanol glucuronide (TCG) in an individual or a solution, the method comprising contacting an in vitro sample taken from the individual or a solution with a conjugate and an antibody that specifically binds to TCG, wherein said antibody generated against an immunogen of the structure

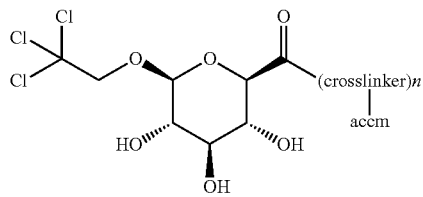

where n=0 or 1; and where, when n=1, the crosslinker joins the carbonyl substituent of the tetrahydropyran ring to an antigenicity conferring carrier material (accm), and said antibody has less than 0.69% cross-reactivity to chloral hydrate, trichloroacetic acid and ethyl glucuronide as compared to reactivity of TCG, detecting the bound conjugate, and deducing from a calibrator value or calibrator values the presence or amount of TCG.

2. The method of claim 1 in which the in vitro sample is urine.

3. The method of claim 1 wherein said antibody is generated against an immunogen of the structure

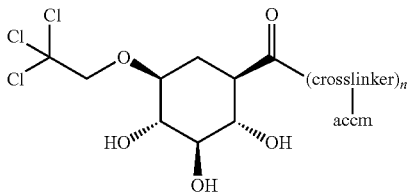

in which n=1 and the crosslinker is —X—Y—Z—,
where X is a heteroatom selected from nitrogen, oxygen or sulphur;
Y is a $C_1$-$C_{10}$ substituted or unsubstituted straight chain alkylene moiety, or arylene moiety; and
Z, before conjugation with the accm, is selected from a carboxy, a dithiopyridyl, a maleimide, an amino, a hydroxyl, a thiol, a thioester or an aldehyde moiety.

4. The method of claim 1 wherein said antibody is generated against an immunogen of the structure

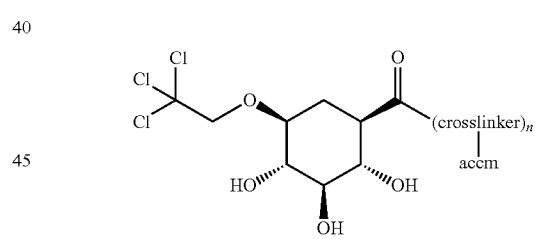

in which n=0 and the accm is selected from bovine serum albumin, egg ovalbumin, bovine gamma globulin, bovine thyroglobulin or keyhole limpet haemocyanin.

5. The method of claim 1 wherein said antibody is generated against an immunogen of the structure

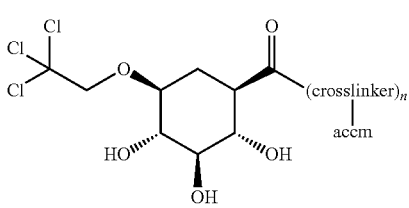

in which n=0 and the accm is bovine thyroglobulin.

* * * * *

UNITED STATES PATENT AND TRADEMARK OFFICE
CERTIFICATE OF CORRECTION

PATENT NO. : 8,530,177 B2
APPLICATION NO. : 13/171599
DATED : September 10, 2013
INVENTOR(S) : Elouard Benchikh It is certified that error appears in the above-identified patent and that said Letters Patent is hereby corrected as shown below:

In the Specification

In column 1, line 34, after Gaullier et, delete "at" and insert --al--
In column 1, line 34, after Engelhart et, delete "at" and insert --al--
In column 2, line 20, delete "know ledge" and insert --knowledge--
In column 2, line 42, delete "at" and insert --al--
In column 2, line 43, delete "at" and insert --al--
In column 2, line 46, delete "at" and insert --al--
In column 2, line 48, delete "at" and insert --al--
In column 2, line 51, delete "at" and insert --al--
In column 3, line 35, after "suphur" delete ":" and insert --;--
In column 3, line 43, after "accm" delete "," and insert --.--
In column 4, line 58, delete "an)" and insert --any--
In column 4, line 65, after "immunoassay" delete ":" and insert --;--
In column 6, line 56, delete "142" and insert --14.2--

Signed and Sealed this
Twenty-fourth Day of December, 2013

Margaret A. Focarino
*Commissioner for Patents of the United States Patent and Trademark Office*